US007906283B2

(12) United States Patent
McMahon et al.

(10) Patent No.: US 7,906,283 B2
(45) Date of Patent: Mar. 15, 2011

(54) METHODS TO IDENTIFY PATIENTS AT RISK OF DEVELOPING ADVERSE EVENTS DURING TREATMENT WITH ANTIDEPRESSANT MEDICATION

(75) Inventors: Francis J. McMahon, Bethesda, MD (US); Gonzalo E. Laje, Potomac, MD (US); Silvia Paddock, Solna (SE); Husseini K. Manji, Cabin John, MD (US); A. John Rush, Dallas, TX (US)

(73) Assignees: The United States of America as represented by the Department of Health and Human Services, Washington, DC (US); Board of Regents, the University of Texas System, Austin, IL (US)

(*) Notice: Subject to any disclaimer, the term of this patent is extended or adjusted under 35 U.S.C. 154(b) by 337 days.

(21) Appl. No.: 11/925,334

(22) Filed: Oct. 26, 2007

(65) Prior Publication Data

US 2008/0102467 A1    May 1, 2008

Related U.S. Application Data

(60) Provisional application No. 60/854,978, filed on Oct. 27, 2006.

(51) Int. Cl.
C12Q 1/68    (2006.01)
C12P 19/34    (2006.01)
C07H 21/02    (2006.01)
C07H 21/04    (2006.01)

(52) U.S. Cl. ........ 435/6; 435/91.2; 536/23.5; 536/24.31

(58) Field of Classification Search .................. None
See application file for complete search history.

(56) References Cited

U.S. PATENT DOCUMENTS

| 7,083,921 B2 | 8/2006 | Murphy et al. |
| 2004/0265825 A1 | 12/2004 | Tartakovsky |
| 2005/0069936 A1 | 3/2005 | Diamond et al. |
| 2006/0160119 A1 | 7/2006 | Turner et al. |
| 2007/0003931 A1 | 1/2007 | Mrazek et al. |
| 2008/0299125 A1 | 12/2008 | Hinds et al. |

OTHER PUBLICATIONS

Halushka et al. Nature. Jul. 1999. 22: 239-247.*
Lucentini et al. The Scientist (2004) vol. 18, p. 20.*
Wacholder et al . J. Natl. Cancer Institute (2004) 96(6):434-442.*
Ioannidis et al. Nature genetics (2001) 29:306-309.*
Kato et al. Neuropsychobiology. 2006.53: 186-195.*
Menke et al. American Journal of Psychiatry. 2008. 165(7): 917-918.*
Laje et al . American Journal of Psychiatry. 2007. 164: 1530-1538.*
GeneCard for the PAPLN gene available via url: <genecards.org/cgi-bin/carddisp.pl?gene=Papln&snp=299#snp>, printed on Dec. 15, 2009.*
GeneCard for the IL28RA gene available via url: <genecards.org/cgi-bin/carddisp.pl?gene=Il28ra&snp=284#snp>, printed on Dec. 15, 2009.*
Thisted, R.A. May 25, 1998; available online via url: <stat.uchicago.edu/~thisted>, pp. 1-6.*
Laje et al. American Journal of Human Genetics. 141B, Issue 7, pp. 724-725, abstract O22.3, available online Sep. 11, 2006.*
Choi et al., *Neuropsychobiology*, 52, 155-162 (2005).
Lipsky et al., *Neuropsychopharmacology*, 31(*No. Suppl. 1*), S23-S24 (2006).
McMahon, *American Journal of Medical Genetics*, 141B(No. 7), 689-690 (2006).
McMahon, *Neuropsychopharmacology*, 31(*No. Suppl. 1*), S38-S39 (2006).
Murphy et al., *American Journal Psychiatry*, 160(10), 1830-1835 (2003).
GenBank Accession No. AAH32004 (Jul. 15, 2006).
GenBank Accession No. AAH37954 (Sep. 1, 2006).
GenBank Accession No. BC032004 (Jul. 15, 2006).
GenBank Accession No. BC037954 (Sep. 1, 2006).
GenBank Accession No. NM_000827 (Sep. 24, 2007).
GenBank Accession No. NM_000828 (Sep. 17, 2007).
GenBank Accession No. NM_000833 (Sep. 25, 2007).
GenBank Accession No. NM_001018064 (Oct. 28, 2007).
GenBank Accession No. NM_006028 (Sep. 3, 2007).
GenBank Accession No. NM_021956 (Oct. 22, 2007).
GenBank Accession No. NM_170743 (Sep. 25, 2007).
GenBank Accession No. NM_173462 (Jun. 26, 2007).
Mann et al., "ACNP Task Force report on SSRIs and suicidal behavior in youth," *Neuropsychopharmacology*, 31 (3), 473-492 (2006).
McMahon et al., "Variation in the gene encoding the serotonin 2A receptor is associated with outcome of antidepressant treatment," *Am. J. Hum. Genet.*, 78, 804-814 (2006).
Rush et al., "Sequenced treatment alternatives to relieve depression (STAR*D): rationale and design," *Control Clin. Trials*, 25 (1), 119-142 (2004).
Trivedi et al., "Evaluation of outcomes with citalopram for depression using measurement-based care in STAR*D: implications for clinical practice," *Am. J. Psychiatry*, 163 (1), 28-40 (2006).

* cited by examiner

*Primary Examiner* — Carla Myers
(74) *Attorney, Agent, or Firm* — Leydig, Voit & Mayer

(57) ABSTRACT

The invention provides a method of screening patients to identify those patients more likely to exhibit an increased risk of treatment-emergent suicidal ideation comprising: (a) obtaining a sample of genetic material from the patients, and (b) assaying the sample for the presence of a genotype in the patients which is associated with an increased risk of treatment-emergent suicidal ideation, wherein the genotype is characterized by a polymorphism in a gene selected from the group consisting of glutamine receptor, ionotropic, kainate 2 (GRIK2); glutamate receptor ionotropic AMPA 3 (GRIA3); and combinations thereof.

4 Claims, No Drawings

METHODS TO IDENTIFY PATIENTS AT RISK OF DEVELOPING ADVERSE EVENTS DURING TREATMENT WITH ANTIDEPRESSANT MEDICATION

CROSS-REFERENCE TO RELATED APPLICATIONS

This patent application claims the benefit of U.S. Provisional Patent Application No. 60/854,978, filed Oct. 27, 2006, which is incorporated by reference.

STATEMENT REGARDING FEDERALLY SPONSORED RESEARCH AND DEVELOPMENT

This invention was made with Government support under Grant N01MH90003 awarded by the National Institutes of Health.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,236 Byte ASCII (Text) file named "702157ST25.TXT," created on Oct. 25, 2007.

BACKGROUND OF THE INVENTION

Depression is a disease that affects a large proportion of the population and is a result of multiple factors. According to the World Health Organization (WHO), depression ranks among the ten leading causes of disability and will become the second-largest cause of the global health burden by 2020. An estimated 121 million people worldwide suffer from a depressive disorder for which they require treatment. It is estimated that 5.8% of all men and 9.5% of all women will suffer from a depressive disorder in any given year and that 17% of all men and women will suffer from a depressive disorder at some point in their lives.

Several types of antidepressant medications are used to treat depressive disorders, such as selective serotonin reuptake inhibitors (SSRIs), tricyclics, and monoamine oxidase inhibitors (MAOIs). The SSRIs and other medications that affect neurotransmitters, such as dopamine and norepinephrine, generally have fewer side effects than tricyclics. However, studies report a potential link between antidepressant use and the emergence of suicidal tendencies. According to some studies suicidal ideation (SI) is an uncommon but potentially dangerous phenomenon that can emerge during antidepressant treatment. Although there is no clear understanding of the basis for the observed linkage, the Food and Drug Administration (FDA) issued a black box warning regarding the potential risk of worsening depression and/or emergence of suicidality (i.e., development of suicidal thoughts or behavior) in both adult and pediatric patients taking several antidepressants.

In view of the FDA's warning, there has been increasing hesitation by physicians to prescribe antidepressants, particularly to children and adolescents. The need exists for a method to identify individuals at risk for developing these dangerous side effects. The invention provides such a method that could provide information about a patient's susceptibility for treatment-emergent suicidal ideation (TESI). These and other objects and advantages of the invention, as well as additional inventive features, will be apparent from the description of the invention provided herein.

BRIEF SUMMARY OF THE INVENTION

The invention provides a method of screening patients to identify those patients more likely to exhibit an increased risk of treatment-emergent suicidal ideation comprising (a) obtaining a sample of genetic material from the patients, and (b) assaying the sample for the presence of a genotype in the patients which is associated with an increased risk of treatment-emergent suicidal ideation, wherein the genotype is characterized by a polymorphism in a gene selected from the group consisting of glutamine receptor, ionotropic, kainate 2 (GRIK2); glutamate receptor ionotropic AMPA 3 (GRIA3); and combinations thereof.

DETAILED DESCRIPTION OF THE INVENTION

The biological basis for treatment emergent suicidal ideation (TESI) following treatment with antidepressants, such as SSRIs, previously was unknown. The inventors have determined that specific genetic markers can shed light on the causes of TESI and help to identify individuals that are at high-risk for TESI and that can benefit from closer monitoring, alternative treatments, and/or specialty care.

The inventors utilized the Sequenced Treatment Alternatives to Relieve Depression (STAR*D) trial, which is a large prospective treatment trial for major depression to test whether specific genetic markers could predict TESI in patients treated with the selective serotonin reuptake inhibitor (SSRI) citalopram.

The inventors identified genetic markers that identify patients at high risk of developing suicidal thoughts during treatment with the SSRI citalopram. The markers reside in the genes glutamine receptor, ionotropic, kainate 2 (GRIK2) and glutamate receptor ionotropic AMPA 3 (GRIA3).

GRIK2 and GRIA3 encode receptors for the excitatory neurotransmitter glutamate. Glutamate receptors are the predominant excitatory neurotransmitter receptors in the mammalian brain and are activated in a variety of normal neurophysiologic processes. These receptors are heteromeric protein complexes with multiple subunits, each possessing transmembrane regions, and all arranged to form a ligand-gated ion channel. The classification of glutamate receptors is based on their activation by different pharmacologic agonists.

GRIK2 encodes a subunit of a kainate glutamate receptor. GRIK2 also is known as EAA4, GLR6, GLUR6, GLuR-6, and GluR-6. GRIK2 is located on chromosome 6q16.3-q21. GRIK2 is identified by GenBank Accession Numbers BC037954 and AAH37954, as well as IMAGE clone 5728492.

GRIA3 belongs to a family of alpha-amino-3-hydroxy-5-methyl-4-isoxazole propionate (AMPA) receptors. Alternative splicing results in several different isoforms which may vary in their signal transduction properties. GRIA3 also is known as GLUR-K3, GLUR3, GLURC, GluR-3, GluR-K3, and gluR-C. GRIA3 is located on chromosome Xq25-q26. GRIA3 is identified by GenBank Accession Numbers BC032004 and AAH32004, as well as IMAGE clone 4753474.

The invention is directed to a method of screening patients to identify those patients more likely to exhibit an increased risk of treatment-emergent suicidal ideation comprising (a) obtaining a sample of genetic material from the patients, and (b) assaying the sample for the presence of a genotype in the patients that is associated with an increased risk of TESI, wherein the genotype is characterized by a polymorphism in a gene selected from the group consisting of GRIK2, GRIA3, and combinations thereof.

TESI refers to the appearance of suicidal thoughts and/or behavior following treatment, such as treatment with SSRIs. For example, suicidal thoughts and behavior include, but are not limited to, the following: feeling that life is empty and/or wondering if life is worth living; thinking of suicide or death several times a week for several minutes; thinking of suicide or death several times a day in some detail; making specific plans for suicide; and attempting or succeeding in taking one's life.

A patient refers to an individual awaiting or under medical care and treatment, such as treatment for depression. While the inventive methods are designed for human patients (e.g., male and female human patients), such methods are applicable to any suitable individual, which includes, but is not limited to, a mammal, such as a mouse, rat, rabbit, hamster, guinea pig, cat, dog, goat, cow, horse, pig, and simian.

The sample of genetic material can be obtained from the patient by any suitable manner. The sample can be isolated from a source including saliva, buccal cells, hair roots, blood, cord blood, amniotic fluid, interstitial fluid, peritoneal fluid, chorionic villus, semen, or other suitable cell or tissue sample. Methods for isolating genomic DNA from various sources is well-known in the art.

A polymorphism refers to one of multiple alleles of a gene. Preferably, the polymorphism is a single nucleotide polymorphism (SNP).

The polymorphism that is associated with an increased risk of TESI can be detected by any suitable manner known in the art. For example, the polymorphism can be detected by techniques, such as allele specific hybridization, allele specific oligonucleotide ligation, primer extension, minisequencing, mass spectroscopy, heteroduplex analysis, single strand conformational polymorphism (SSCP), denaturing gradient gel electrophoresis (DGGE), oligonucleotide microarray analysis, temperature gradient gel electrophoresis (TGGE), and combinations thereof.

The polymorphism that is associated with an increased risk of TESI in the GRIK2 gene typically is within intron 1 of GRIK2 (GenBank Accession Number NM_021956). In such a situation, intron 1 of GRIK2 typically comprises SEQ ID NO: 1, which contains a cytosine at position 201, rather than adenine (which is present in the GRIK2 intron 1 that is not associated with an increased risk of TESI). This adenine/cytosine SNP is associated with marker rs2518224 at chromosome 6:102013370.

The polymorphism that is associated with an increased risk of TESI in the GRIA3 gene typically is within intron 3 of GRIA3 (GenBank Accession Number NM_000828). In such a situation, intron 3 of GRIA3 typically comprises SEQ ID NO: 2, SEQ ID NO: 3, or SEQ ID NO: 13. SEQ ID NO: 2 contains a thymine at position 201, rather than adenine (which is present in the GRIA3 intron 3 that is not associated with an increased risk of TESI). This adenine/thymine SNP is associated with marker rs6608067 at chromosome X:122151011. SEQ ID NO: 3 contains a guanine at position 201, rather than adenine (which is present in the GRIA3 gene that is not associated with an increased risk of TESI). This adenine/guanine SNP is associated with marker rs4825476 at chromosome X:122167014. SEQ ID NO: 13 contains a thymine at position 201, rather than cytosine (which is present in the GRIA3 intron 3 that is not associated with an increased risk of TESI). This cytosine/thymine SNP is associated with marker rs5911588 at chromosome X:122286074.

The invention also comprises assaying for the presence of a genotype that is associated with an increased risk of TESI, wherein the genotype is characterized by a polymorphism in a gene selected from the group consisting of: glutamate receptor, ionotropic, N-methyl D-aspartate (GRIN) 2A; neurotrophic tyrosine receptor kinase (NTRK) 2; 5-hydroxytryptamine (serotonin) receptor (HTR) 3B; GRIA1; papilin (PAPLN); interleukin 28 receptor alpha (IL28RA); and combinations thereof. Certain polymorphisms in these genes correlate with an increased risk of developing suicidal thoughts during treatment with the SSRI citalopram.

The polymorphism that is associated with an increased risk of TESI in GRIN2A typically is within intron 3 of GRIN2A (GenBank Accession Number NM_000833). In such a situation, intron 3 of GRIN2A typically comprises SEQ ID NO: 4, which contains a cytosine at position 201, rather than adenine (which is present in the GRIN2A gene that is not associated with an increased risk of TESI). This thymine/guanine SNP (opposite strand) is associated with marker rs3104703 at chromosome 16:9972637.

The polymorphism that is associated with an increased risk of TESI in NTRK2 typically is within intron 14 of NTRK2 (GenBank Accession Number NM_001018064). In such a situation, intron 14 of NTRK2 typically comprises SEQ ID NO: 5, which contains a guanine at position 201, rather than adenine (which is present in the NTRK2 gene that is not associated with an increased risk of TESI). This cytosine/thymine SNP (opposite strand) is associated with marker rs1573219 at chromosome 9:84617176.

The polymorphism that is associated with an increased risk of TESI in HTR3B typically is within intron 6 of HTR3B (GenBank Accession Number NM_006028). In such a situation, intron 6 (boundary) of HTR3B typically comprises SEQ ID NO: 6, which contains a guanine at position 201, rather than adenine (which is present in the HTR3B gene that is not associated with an increased risk of TESI). This adenine/guanine SNP (opposite strand) is associated with marker rs2276307 at chromosome 11:113309097.

The polymorphism that is associated with an increased risk of TESI in GRIA1 typically is within intron 5 of GRIA1 (GenBank Accession Number NM_000827). In such a situation, intron 5 of GRIA1 typically comprises SEQ ID NO: 7, which contains a cytosine at position 201, rather than adenine (which is present in the GRIA1 gene that is not associated with an increased risk of TESI). This adenine/cytosine SNP is associated with marker rs4958672 at chromosome 5:153028245.

The polymorphism that is associated with an increased risk of TESI in PAPLN typically is within intron 13 of PAPLN (GenBank Accession Number NM_173462). In such a situation, intron 13 (boundary) of PAPLN typically comprises SEQ ID NO: 8, which contains a guanine at position 201, rather than adenine (which is present in the PAPLN gene that is not associated with an increased risk of TESI). This adenine/guanine SNP is associated with marker rs2293796 at chromosome 14:72790915. Similarly, in such a situation, intron 13 (boundary) of PAPLN can comprise SEQ ID NO: 9, which contains a thymine at position 201, rather than a cytosine (which is present in the PAPLN gene that is not associated with an increased risk of TESI). This cytosine/thymine SNP is associated with marker rs11628713 at chromosome 14:72791528.

The polymorphism that is associated with an increased risk of TESI in IL28RA typically is within exon 7 or intron 4 of IL28RA (GenBank Accession Number NM_170743). In such a situation, exon 7 of IL28RA typically comprises SEQ ID NO: 10, which contains a guanine at position 201, rather than adenine (which is present in the IL28RA gene that is not associated with an increased risk of TESI). This adenine/guanine SNP is associated with marker rs10903034 at chromosome 1:24226211. Similarly, exon 7 of IL28RA can comprise SEQ ID NO: 11, which contains a thymine at position 201, rather than cytosine (which is present in the IL28RA gene that is not associated with an increased risk of TESI). This cytosine/thymine SNP is associated with marker rs11249006 at chromosome 1:24227780. Similarly, in such a situation, intron 4 of IL28RA typically comprises SEQ ID NO: 12, which contains thymine at position 201, rather than cytosine (which is present in the IL28RA gene that is not associated with an increased risk of TESI). This cytosine/thymine SNP is associated with marker rs1416834 at chromosome 1:24231966.

Sensitivity is the probability that a symptom is present (or the screening test is positive) when a patient has a disorder. The sensitivity of the polymorphism associated with TESI in the inventive method can be any suitable sensitivity. Preferably, the sensitivity is about 0.5 or higher (e.g., about 0.55, about 0.6, about 0.65, about 0.7, about 0.75, about 0.8, about 0.85, about 0.9, about 0.95, and ranges thereof).

Specificity is the probability that a symptom is not present (or the screening test is negative) when a patient does not have a disorder. The specificity of the polymorphism associated with TESI in the inventive method can be any suitable specificity. Preferably, the specificity is about 0.5 or higher (e.g., about 0.55, about 0.6, about 0.65, about 0.7, about 0.75, about 0.8, about 0.85, about 0.9, about 0.95, and ranges thereof).

Positive predictive value is the probability that a patient has a disorder given a positive test result. The positive predictive value of the polymorphism associated with TESI in the inventive method can be any suitable value. Preferably, the positive predictive value is about 0.05 or higher (e.g., about 0.1, about 0.2, about 0.25, about 0.3, about 0.4, about 0.5, about 0.55, about 0.6, about 0.65, about 0.7, about 0.75, about 0.8, about 0.85, about 0.9, about 0.95, and ranges thereof).

Negative predictive value is the probability that a patient has the disorder given a negative test result. The negative predictive value of the polymorphism associated with TESI in the inventive method can be any suitable value. Preferably, the negative predictive value is about 0.5 or higher (e.g., about 0.55, about 0.6, about 0.65, about 0.7, about 0.75, about 0.8, about 0.85, about 0.9, about 0.95, and ranges thereof).

The invention also contains a kit comprising reagents suitable for applying the methods of the invention. The kit provides the necessary materials for identifying the polymorphism packaged into a suitable container. At a minimum, the kit contains a reagent that identifies a polymorphism in the selected gene that is associated with a selected trait, such as TESI. Preferably, the reagent is a set of primers or a PCR set (a set of primers, DNA polymerase, and 4 nucleoside triphosphates) that hybridizes with the gene or a fragment thereof. The kit also can include other reagents for detecting or measuring the detectable entity and/or a control. Other reagents used for hybridization, prehybridization, DNA extraction, visualization, and the like also can be included.

The following example further illustrates the invention but, of course, should not be construed as in any way limiting its scope.

Example

This example demonstrates that genetic markers can be used to identify individuals with a major depressive disorder who develop treatment-emergent suicidal ideation (TESI) when exposed to a selective-serotonin reuptake inhibitor (SSRI), such as citalopram.

Experimental Design

DNA was collected from a clinically-representative cohort of 1938 outpatients with major depressive disorder enrolled in the Sequenced Treatment Alternatives to Relieve Depression (STAR*D) trial. Outpatients 18-75 years of age with a baseline 17-item Hamilton Depression Rating Scale (see Hamilton et al., *J. Neurol. Neurosurg. Psychiatry*, 23: 56-62 (1960); and Hamilton, *Br. J. Soc. Clin. Psychol.*, 6(4): 278-296 (1967)) (HRSD17) score of $\geq 14$ who met the Diagnostic and Statistical Manual of Mental Disorders (DSM)-IV criteria for non-psychotic major depressive disorder (MDD) were eligible for the trial.

All participants received initial therapy with citalopram, typically starting at 20 mg/day, with dose increases following recommended procedures (see Trivedi et al., *Am. J. Psychiatry*, 163(1): 28-40 (2006)). The patients were treated with citalopram under a standard protocol for up to 14 weeks. DNA was extracted from whole blood and genotyped on an Illumina Bead Array platform (see Gunderson et al., *Genome Res.*, 14(5): 870-877 (2004)) for 768 single nucleotide polymorphisms (SNPs) in 68 candidate genes. Genes were selected to sample five broad signaling pathways of potential importance in antidepressant effects: serotonin (20 genes), glutamate (16 genes), dopamine (3 genes), norepinephrine (4 genes), and neurotrophins (4 genes), as well as selected genes in other pathways (21 genes). All probands with TESI and a subset of probands without TESI were also screened with the Illumina 109K Exon-Centric chip, which measures the genotype of a DNA sample at each of 109,000 SNPs in and near most known human genes.

The 16-item Quick Inventory of Depressive Symptomatology—Self-report ($QIDS-SR_{16}$) was used as a measure of symptom severity (see Rush et al., *Int. J. Methods Psychiatr. Res.*, 9: 45-59 (2000): Rush et al., *Biol. Psychiatry*, 54(5): 573-583 (2003); Trivedi et al., *Psychol. Med.*, 34(1): 73-82 (2004); Rush et al., *Neuropsychompharmacology*, 30(2): 405-416 (2005); and Rush et al., *Biol. Psychiatry*, 59(6): 493-501 (2006)) and was obtained at baseline and at each bi-weekly clinic visit. TESI was defined by responses to item 12 of the $QIDS-SR_{16}$ ("Thoughts of death or suicide"). Possible responses include: "I do not think of suicide or death" (=0), "I feel that life is empty or wonder if it's worth living" (=1), "I think of suicide or death several times a week for several minutes" (=2), and "I think of suicide or death several times a day in some detail, or I have made specific plans for suicide, or have actually tried to take my life (=3). Participants who scored "0" on this item before citalopram treatment, but who scored 1, 2, or 3 on the same item at least once while receiving citalopram were defined as TESI cases (n=120). The comparison group (n=1742) consisted of all participants who denied suicidal ideation emerging during treatment. This included participants who denied suicidal ideation at the initial and subsequent visits (n=765), as well as those who admitted to suicidal ideation at the initial visit before commencing treatment, whatever their subsequent report (n=977). Participants missing suicidal ideation data (n=53) were excluded.

Statistical Analysis

Allele and genotype frequencies were compared between the 120 participants who developed TESI and those who did not develop TESI. Allele-wise tests are most powerful for alleles that confer risk in a co-dominant or dominant fashion, while genotype-wise tests are more powerful when a recessive model applies. Allele-wise comparisons were performed with Cocaphase in the UNPHASED package (see Dudbridge et al., *Am. J. Hum. Genet.*, 75(3): 424-435 (2004)), which estimates a likelihood-based test of association under the null hypothesis of all odds ratios (ORs) being equal to one. Genotype-wise comparisons were carried out using a Pearson Chi-square test on a 2×3 contingency table. Experiment-wise p-values were estimated by permuting case-control labels 10,000 times. The number of p-values less than or equal to the lowest p-value observed in the actual data were tallied. Permutation tests were run separately for autosomal and X-linked markers. Hardy-Weinberg equilibrium for the chosen markers was calculated using PEDSTATS (see Wegginton et al., *Bioinformatics*, 21(16): 3445-3447 (2005)).

SNPs that passed the initial tests with an experiment-wise p<0.05 were studied further. Tests of association included a logistic regression model calculated with SAS 9.1.3 Enterprise Guide 3.0 (SAS Institute, Cary, N.C.), with a nominal dependent variable for TESI. X-linked markers were separately analyzed in males and females. Single marker tests were carried out under co-dominant, dominant, and recessive models. Models were compared by the Likelihood Ratio Test (LRT). The best-fitting model was used for the multi-marker analyses. The reference model was based on the SNPs with the largest identified ORs in the single marker models. The remaining covariates were added in a step-wise fashion in descending order of OR. The 2 log-likelihood (−2 Log L) was used to assess the improvement of fit as each variable was removed from the model. The Hosmer-Lemeshow test was used to test for final model fit.

Cases and controls were characterized clinically using bivariate methods. Differences between groups were tested by Chi-square statistics for nominal and ordinal variables and by t-statistics for continuous variables.

Results

Two markers were significantly associated with TESI. A marker in the gene GRIK2 on chromosome 6 (marker 157), which encodes the type 6 glutamate receptor, was associated with TESI in the genotype-wise test (nominal p=$2.43\times10^{-5}$; permutation p<0.003). This marker was not significantly associated in the allele-wise test, but three other markers in this gene produced nominally-significant evidence of allelic association.

A second marker, in the gene GRIA3 on chromosome X (marker 239), which encodes an AMPA receptor, was associated with TESI in the allele-wise test (nominal p=$7.84\times10^{-5}$; permutation p<0.01). The genotype-wise test of this marker also produced nominally-significant evidence of association in females (p=0.0062), as did allele-wise tests of four nearby markers in this gene.

Having established experiment-wise significant associations between the two markers and TESI, the impact of non-genetic variables, such as race, on the observed genetic association was investigated. Table 1 includes demographic and clinical data for the 120 participants and the 1742 controls.

TABLE 1

Demographic and Clinical Data.

| Variable | Cases (n = 120) N (%) | Controls (n = 1742) N (%) | df | $\chi^2$ | p |
|---|---|---|---|---|---|
| Gender (female) | 71 (59.2) | 1072 (61.5) | 1 | 0.2664 | NS[a] |
| Race | | | 2 | 1.0563 | NS |
| White | 91 (75.8) | 1382 (79.3) | | | |
| Black | 20 (16.7) | 262 (15.0) | | | |
| Other | 9 (7.5) | 98 (5.6) | | | |
| Hispanic (No) | 102 (85.0) | 1501 (86.2) | 1 | 0.1273 | NS |
| Employment | | | 2 | 1.9630 | NS |
| Employed | 64 (53.3) | 981 (56.3) | | | |
| Retired | 6 (5.0) | 129 (7.4) | | | |
| Unemployed | 50 (41.7) | 632 (36.3) | | | |
| Marital status | | | 3 | 0.6588 | NS |
| Married | 52 (43.3) | 745 (42.8) | | | |
| Divorced | 33 (27.5) | 435 (25.0) | | | |
| Never Married | 31 (25.8) | 492 (28.2) | | | |
| Widowed | 4 (3.3) | 70 (4.0) | | | |

| Clinical Characteristics - Categorical | Cases (n = 120) N (%) | Controls (n = 1742) N (%) | df | $\chi^2$ | p |
|---|---|---|---|---|---|
| Remission by QIDS-C[b] (No) | 90 (75.6) | 994 (57.2) | 1 | 15.529 | <0.0001 |
| Psychomotor Agitation (No) (QIDS-SR$_{16}$ item 16) | 104 (86.7) | 1508 (86.6) | 1 | 0.0010 | NS |
| Initial Insomnia (No) (QIDS-SR$_{16}$ item 1) | 104 (86.7) | 1530 (87.8) | 1 | 0.1414 | NS |
| Drug Abuse (No)[c] | 109 (93.2) | 1618 (94.0) | 1 | 0.1404 | NS |
| Alcohol Abuse (No)[c] | 105 (89.0) | 1543 (89.5) | 1 | 0.0254 | NS |
| History of Suicide Attempts (No) | 101 (84.2) | 1481 (85.1) | 1 | 0.0713 | NS |
| Medication Tolerability[d] | | | 3 | 3.1386 | NS |
| Intolerant | 12 (10.1) | 198 (11.4) | | | |
| Probably Intolerant | 2 (1.7) | 34 (1.9) | | | |
| Probably Tolerant | 26 (21.9) | 273 (15.7) | | | |
| Tolerant | 79 (66.4) | 1232 (70.9) | | | |
| Level 1 exit | | | 2 | 14.834 | 0.0006 |
| Follow Up | 35 (29.2) | 805 (46.2) | | | |
| Next Level | 75 (62.5) | 782 (44.9) | | | |
| Study Exit | 10 (8.3) | 155 (8.9) | | | |

TABLE 1-continued

Demographic and Clinical Data.

| Clinical characteristics - Continuous | Cases (n = 120) Mean (SD) | Controls (n = 1742) Mean (SD) | t | p |
|---|---|---|---|---|
| Maximum Citalopram Dose (mg/d) | 51.75 (13.7) | 46.22 (15.3) | 3.86 | 0.0001 |
| Age at Onset of First MDE (yrs.) | 24.31 (15.8) | 25.89 (15.0) | −1.12 | NS |
| Age at enrollment (yrs.) | 42.26 (13.3) | 42.54 (13.4) | −0.22 | NS |

[a] Not significant
[b] Defined as score of 5 or less on the last recorded visit.
[c] Based on self-report responses to the Psychiatric Diagnostic Screening Questionnaire set at 90% specificity (see Rush et al., J. Affect Disord., 87(1): 43-55 (2005)).
[d] As defined by the algorithm detailed in McMahon et al. (Am. J. Hum. Genet., 78(5): 804-814 (2006)).

The best-fitting model was achieved with a combination of both markers, maximum citalopram dose, and remission by the 16-Item Quick Inventory of Depressive Symptomatology (QIDS)-Clinician Rating (QIDS-C). Race was not a significant covariate in this model. Adjusted ORs were very close to those in the unadjusted models. The Hosmer-Lemeshow test was non-significant for both genders, indicating a good model fit.

Tables 2 and 3 demonstrate logistic regression models with stepwise selection for the two markers, wherein race was forced into each model.

TABLE 2

Logistic Regression Model for Females (n = 70 cases, 1067 controls).

| Step | Model variables | −2Log L | LR$\chi^2$ | df | p-value |
|---|---|---|---|---|---|
| 1 | marker 157 and race | 519.6 | 6.3 | 3 | 0.0982 |
| 2 | marker 157, remission, race | 512.2 | 13.7 | 4 | 0.0084 |
| 3 | marker 157, marker 239, remission, race | 505.2 | 20.7 | 5 | 0.0009 | wherein LR = likelihood ratio, df = degrees of freedom. The c index for this model is 0.64.

TABLE 3

Logistic Regression Model for Males (n = 49 cases, 670 controls).

| Step | Model variables | −2Log L | LR$\chi$2 | df | p-value |
|---|---|---|---|---|---|
| 1 | marker 157 and race | 346.5 | 11.3 | 3 | 0.01 |
| 2 | marker 157, maximum citalopram dose, race | 334.1 | 23.8 | 4 | <.0001 |
| 3 | marker 157, maximum citalopram dose, marker 239, race | 327.8 | 30.1 | 5 | <.0001 |
| 4 | marker 157, marker 239, maximum citalopram dose, remission, race | 323.0 | 34.8 | 6 | <.0001 |

The c index for this model is 0.73.

The clinical parameters for markers 157 and 239 are reported in Table 4. The high-risk genotype of marker 157 correlates with a SNP in intron 1 of GRIK2 (e.g., SEQ ID NO: 1). The high-risk alleles of marker 239 contain a SNP in intron 3 of GRIA3 (e.g., SEQ ID NOs: 2 and 3). Of the six combinations of high-risk alleles and genotypes tested, the highest OR was observed in patients carrying both the high-risk alleles of marker 239 and the high-risk genotype of marker 157 (OR=14.98, 95% Confidence Interval (CI)=3.7, 60.674). Although only 8 patients carried it, this particular combination of alleles had 99.8% specificity for TESI. The most sensitive test (57%) required the presence of one or more high-risk alleles of marker 239 only. The combined impact of both markers on TESI risk appears to be at least additive, but sample size precludes any precise estimates of the mode of interaction.

TABLE 4

Clinical parameters for Markers 157 and 239.

| Model | OR | 95% CI | Sensitivity | Specificity | Positive Predictive Value | Negative Predictive Value | Prevalence Ratio |
|---|---|---|---|---|---|---|---|
| (1) marker 157, high-risk genotype | 8.23 | 3.224, 21.057 | 0.06 | 0.993 | 0.35 | 0.94 | 5.71 |
| (2) marker 239, ≧one high-risk allele | 1.94 | 1.33, 2.82 | 0.57 | 0.59 | 0.09 | 0.95 | 1.85 |
| (3) marker 239, two high-risk alleles | 2.19 | 1.45, 3.32 | 0.29 | 0.84 | 0.11 | 0.95 | 2.06 |
| Both (1) and (2) | 8.55 | 2.47, 29.62 | 0.03 | 0.996 | 0.36 | 0.94 | 5.82 |
| Either (1) or (3) | 2.38 | 1.59, 3.57 | 0.32 | 0.84 | 0.12 | 0.95 | 2.22 |
| Both (1) and (3) | 14.9 | 3.70, 60.67 | 0.033 | 0.998 | 0.50 | 0.94 | 7.99 |

The identified markers, taken together, predict TESI in this sample with high specificity, but only moderate sensitivity. This is not surprising given the relatively small number of genes tested and the likely contribution of non-genetic factors to TESI risk. Nevertheless, the findings have several direct clinical implications.

These markers can help identify patients at high risk for TESI. Such patients will benefit from closer monitoring, alternative treatments, and/or specialty care. Such testing can allay the concern that has led regulatory agencies to issue warnings that contribute to a decrease in antidepressant prescriptions for patients who could benefit from them. Rather than broad warnings that can inappropriately affect antidepressant prescribing practices, identification of these markers indicates that narrower warnings could be appropriate that better capture the heterogeneous nature of TESI risk in those patients treated with antidepressants. These findings suggest that at least some of that heterogeneity has a genetic basis.

Several other markers were identified that correlate with an increased risk of TESI. These markers were identified in the following genes: GRIN2A, NTRK2, HTR3B, GRIA1, and PAPLN. SNPs in intron 3 of GRIN2A (e.g., SEQ ID NO: 4), intron 14 of NTRK2 (e.g., SEQ ID NO: 5), intron 16 of HTR3B (e.g., SEQ ID NO: 6), intron 5 of GRIA1 (SEQ ID NO: 7), and intron 13 of PAPLN (e.g., SEQ ID NOs: 8 or 9) were associated with increased risk of TESI in those treated with citalopram.

In particular, markers in PAPLN (marker rs11628713) and IL28RA (marker rs10903034) were significant at the p=0.01 and p=0.06 levels, respectively, in an evaluation of 90 TESI cases and 90 matched controls.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of screening human patients to identify those patients more likely to exhibit an increased risk of treatment-emergent suicidal ideation after treatment with a selective serotonin reuptake inhibitor (SSRI) and detecting the presence of a genotype in the patients which is associated with an increased risk of treatment-emergent suicidal ideation (TESI) after treatment with a SSRI comprising:

(a) obtaining a sample of genetic material from the patients, (b) assaying the sample for the presence of a genotype in the patients which is associated with an increased risk of treatment-emergent suicidal ideation after treatment with a SSRI by performing an assay suitable for detection of a polymorphism, and (c) identifying those patients more likely to exhibit an increased risk of treatment-emergent suicidal ideation after treatment with a SSRI based on the presence of the genotype associated with an increased risk of treatment-emergent suicidal ideation in (b), wherein the genotype is characterized by a polymorphism in each of the following genes: glutamine receptor, ionotropic, kainate 2 (GRIK2); glutamate receptor ionotropic AMPA 3 (GRIA3); glutamate receptor, ionotropic, N-methyl D-aspartate 2A (GRIN2A); neurotrophic tyrosine receptor kinase 2 (NTRK2); 5-hydroxytryptamine (serotonin) receptor 3B (HTR3B), glutamate receptor ionotropic AMPA 1 (GRIA1); papilin (PAPLN); and interleukin 28 receptor alpha (IL28RA);

wherein when the gene is GRIK2, the polymorphism is located within intron 1 of GRIK2, and the polymorphism is the cytosine allele of marker rs2518224;

wherein when the gene is GRIA3, the polymorphism is located within intron 3 of GRIA3, and the polymorphism is the guanine allele of marker rs4825476;

wherein when the gene is GR1N2A, the polymorphism is located within intron 3 of GRIN2A, and the polymorphism is the cytosine allele of marker rs3104703;

wherein when the gene is NTRK2, the polymorphism is located within intron 14 of NTRK2, and the polymorphism is the guanine allele of marker rs1573219;

wherein when the gene is HTR3B, the polymorphism is located within intron 6 of HTR3B, and the polymorphism is the guanine allele of marker rs2276307;

wherein when the gene is GRIA1, the polymorphism is located within intron 5 of GRIA1, and the polymorphism is the cytosine allele of marker rs4958672;

wherein when the gene is PAPLN, the polymorphism is located within intron 13 of PAPLN, and the polymorphism is the thymine allele of marker rs11628713;

wherein when the gene is IL28RA, the polymorphism is located within exon 7 of IL28RA, and the polymorphism is the guanine allele of marker rs10903034.

2. The method of claim 1, wherein assaying comprises detecting the polymorphism by allele specific hybridization, allele specific oligonucleotide ligation, primer extension, minisequencing, mass spectroscopy, heteroduplex analysis, single strand conformational polymorphism (SSCP), denaturing gradient gel electrophoresis (DGGE), oligonucleotide microarray analysis, or temperature gradient gel electrophoresis (TGGE), or combinations thereof.

3. The method of claim 1, wherein assaying for the presence of the genotype comprises detecting the presence of at least one or more of the following polynucleotide sequences including SEQ ID NO: 1, SEQ ID NO: 3, SEQ ID NO: 4, SEQ ID NO: 5, SEQ ID NO: 6, SEQ ID NO: 7, SEQ ID NO: 9, SEQ ID NO: 10, or combinations thereof.

4. The method of screening of claim 1, wherein the human patients are identified after treatment with the SSRI, citalopram.

* * * * *

SEQUENCE LISTING

<160> NUMBER OF SEQ ID NOS: 13

<210> SEQ ID NO 1
<211> LENGTH: 402
<212> TYPE: DNA
<213> ORGANISM: Homo sapiens

<400> SEQUENCE: 1

```
ggcactgcag atacaaaact ccatctgggg tcaggatctt ttccatatta tctgcctggc    60
acaaaagagt gctggcaaac ccagtccacc tctgctagac aatcgtatct ggtactagga   120
cggcagcctc ttcagcaaga aggggtaca ttggccaatt cctatgaatt gggctcctcg    180
tgaagaactc atttatccac ctggagtagg tattaccatg tcaaatttt ctcaaaacat    240 aggacctctc atttcatgag gccaaagatt tcttgatttt aaactgactt ttaatccatg   300
agaatatggc ttgtattaat ttaaaaagta aaagtgttca aactgtgatt gaatcttttt   360
tgtgattatg accgcaaayt tctgtgactt caatattttc ay                      402
```

<210> SEQ ID NO 2
<211> LENGTH: 402
<212> TYPE: DNA
<213> ORGANISM: Homo sapiens

<400> SEQUENCE: 2

```
agagaagaag gcaagagttg aaaaactgtt gggtgctatg ctcagtacct gggtggccaa    60
agcaatcata ccccaagctt cagcatcaca caatatacaa acctgcacat gtaccsctga   120
atctcaaata aaagttgaaa ttattttaa aaaagaaaa gaaaaaagt acaatttta      180 agagaaagta taaagaata tcatcaaga cctaagctct tccttttgc ttctccatcc    240 ttatcayctg gctttcacct atatgcttgt tcccattca catctcgttt gccagaacta   300
tattgcatgg cccgcctcct caatatcagt tgcaagggag cctgggaaac aaagtatcta   360
gctgggcaca ttgccacctt aaacaaaacc aggattgtgt ty                    402

<210> SEQ ID NO 3
<211> LENGTH: 402
<212> TYPE: DNA
<213> ORGANISM: Homo sapiens

<400> SEQUENCE: 3
tggtaggatt tgatatggga ttcagggaat gtattctttg ggaacaatca ctggaggcaa    60
aactttggga gcatttaaaa aactggaagc aaatagcagc acttcaagca gggcagagac   120
acaactaagg ggaagcaatt ctacagttct tcctctgatg actttaactg tccttttcccc  180 acctctgagc aggttttaga gtttcatatc agatgcccag gcagatagga ctgatgactg   240
tcctctggat ctcttgcccc tccctactct aggattcagt ccagcatctt cactacatgc   300
agcccttcct acctacctgt gtgggaagcc actgtgcgct gtagtctcgg tgccaagaat   360
tcgttggcta cagacctttg tgagcctcca tggctgatag gy                    402

<210> SEQ ID NO 4
<211> LENGTH: 402
<212> TYPE: DNA
<213> ORGANISM: Homo sapiens

<400> SEQUENCE: 4
gctgcatgta ataacagctg aggctacagt tccctgagag cacagttggg ctgaaatgta    60
tgagatggct catgacatgg ctaagtggat ggagctggct attggcttgg gggcgtagct   120
cactgcctaa tgtaaccttt ttatgtggct tggatttcac aaagcatggt ggttgagttt   180
tgagttgaca tacccaaggg caattgttat atcagggaag aagtggaagc ttctgtttta   240
ctgaaaatta ggcttttwta ttggtcacat agtcactgtg ctggtcagat tcaagaggag   300
aataaagcaa tccacctgtc aatgggaaga ataacagaaa acagtgtggg catccttaat   360
tcaccccacc tcatactgtc tgctcttatt tgtcacccat ay                    402

<210> SEQ ID NO 5
<211> LENGTH: 402
<212> TYPE: DNA
<213> ORGANISM: Homo sapiens

<400> SEQUENCE: 5
caaggtgctg ataaacattt tactgagcat gtacaatatg ccagccacag ggaatctaca    60
tgtgtacatc atacctgtgt gatgtacctc tagaagtttg tagtctagag gaggcctgac   120
atcccagcag cttctatggt ggctaatgta agaagcccca caaagaggg ggatgattca    180 ttgtctacag aaatcaggga gttcttcaca gcagagtcca ccytccagtg gggtctgaaa   240
gagtgagtaa gagatctctg cacagacgag atggagaagg aggcagtgtt acttactgag   300
gcatgaaggc tcgtgttggg gtggcatgga tattgatgga gtgtaagata tgagagaaca   360
gtggcagggg acgatgatgg agagacagac aagggtcaag gy                    402
```

<210> SEQ ID NO 6
<211> LENGTH: 402
<212> TYPE: DNA
<213> ORGANISM: Homo sapiens

<400> SEQUENCE: 6

```
agcccagaag acattcagca tgacaaaaag gcgtttttga atgacagtga gtgggaactt    60
ctatctgtgt cctccacata cagcatcctg cagagcagcg ctggaggatt tgcacagatt   120
cagtttaatg taggttcttt actacctgtc cccgttgccc gcttctcccc agcctttggc   180
cttctctctt gggccaagga gtttctgctc tattgcatgt tctcattcat tatcacccaa   240
gaacagggac ttcagcgggc tctgagcatc cacctgcatt ccagcatttts acagagcaga   300
ggttcagtgg gagatgctgg gcccctccag aagataacag acaccagagg cctggtattc   360
agacaccaga ggcctgaagc atgccctgca gcaggaatcc ty                      402
```

<210> SEQ ID NO 7
<211> LENGTH: 402
<212> TYPE: DNA
<213> ORGANISM: Homo sapiens

<400> SEQUENCE: 7

```
aatctttgct cctgtatagg tcaaaagtca gcaaactatg gtccctgtgt caaatccagc    60
catcacctga ttttatatgg ctcatgagct aagaatgatt ttttacattt tttaattgtt   120
gggaaaaaaa tcaaaagaat gatattttat aatatgtgga actatatgac attaaaattac  180
catgcccaaa atattggga cagccatgct cttccaatta ctatatgcta aatagtaata   240
gtaaattact attttctata tatggctact ttcatgctgc aatggcagag ctgactagtt   300
gtgacaagaa cyatatggtt tgcaaagcct aaaatattta taatctggcc ctttacataa   360
aaagtttgct gaccccttgc atagatgtgg aataggsgga cy                      402
```

<210> SEQ ID NO 8
<211> LENGTH: 402
<212> TYPE: DNA
<213> ORGANISM: Homo sapiens

<400> SEQUENCE: 8

```
attgcttcta gcacctacgt atattcaagt tgcaaatgga tggaaaatac aaatgggtga    60
caacctcagt ctgttgtcag tagccatggt tcaggctgtg tgacctcagg ggagtgagtc   120
agcctctctg ggcctgggaa ggacatgggc agttgggtgc tatctgcctc cacaccaggc   180
tggtgggccg ctagctgtcc gaactggcgt ggctcctggg ggcaaggccg agcttctgct   240
gacagccttg tccttgcagt gttctgtcag ttgtggcgtt ggcrtccgga agcggagcgt   300
tacttgccgg ggtgaaaggg gttctttgct ccataccgya gcgtgctcct tggaagaccg   360
gccacctctg actgagccct gtgtgcatga ggactgcccc cy                      402
```

<210> SEQ ID NO 9
<211> LENGTH: 402
<212> TYPE: DNA
<213> ORGANISM: Homo sapiens

<400> SEQUENCE: 9

```
tgggyctcag tgctccaaga gctgcagctc gggcactcgg aggcgacagg tcatctgtgc    60
cattgggccg cccagccact gcgggagcct gcagcactcc aagcctgtgg atgtggagcc   120
ttgtaacacg cagccctgtc atctccccca gggtaaggac aggagggcag ggaggagtcc   180
```

```
ggcctctgac ctctctccca ttcgctacaa acccagcaag catgtcctgc ctcggggcct      240
ctgcctgcac tgtgtcatcc ctctggaccc cacttctccc atgtctcccc ccgctgaacc      300 cttttgccatc tctaaggccc acctggtgtg cagcccacca ggcagccctg ctttcctcca     360
ctcagcggta gcatgcccct gcccctctgg cccccatagc ay                        402
```

<210> SEQ ID NO 10
<211> LENGTH: 401
<212> TYPE: DNA
<213> ORGANISM: Homo sapiens

<400> SEQUENCE: 10

```
ttactatttt tttaaagaat tttttccaga gtttaatttc tgacatagct taagttttcc      60
agtaactcta aactccatct cctttatcgt cattaagtca ttcacaaaaa gccaggagaa     120
gcatttggaa agggcatgat aatcagtata ataatttgcr ttgtgtggtc agcacttaac     180
tgtttacaaa gcccttttcac gtgcacagca ggtgggaact gcgcggtgtg ggctgggcct    240
gcgctggaag catatcccgt gaaaagtgtt agtgccttag gtgaaagcaa catgtatccc     300
tttagactac taacggtata tgttgttctt atgtatttgt atttatttct attttttcta     360
tgtttatgtc atatttaaac gatatcctac tgcttgttgg t                        401
```

<210> SEQ ID NO 11
<211> LENGTH: 401
<212> TYPE: DNA
<213> ORGANISM: Homo sapiens

<400> SEQUENCE: 11

```
ctcagaagcc agagcccccac ccaaggggac cctggtctct ccgccttcac ctagcaatgg     60
gaaccctgct tcccagggga ggaaccaact gctccacctt ctagggaccc agtttgttgg    120
agtaggacag taacatggca ggaatcggac ttctgggcct gtaatcccag tttggatggc    180
acgttagact cttggttgac tgttgtggtc cttagaagtc ccattctccc ttccagttat    240
gagaaaccaa tgccttctag attcaggtga ctatccttac ctgggggtgc tgatgcatcc    300
tcagttaacc tacacccacc tgaatataga tgagcgtagc tgagttttca cccgtaggac    360
cgaagtgttt tgtggtggag tatctgaaca accttggctc t                       401
```

<210> SEQ ID NO 12
<211> LENGTH: 401
<212> TYPE: DNA
<213> ORGANISM: Homo sapiens

<400> SEQUENCE: 12

```
cttttttcact acgtctttaa aatctgatgt gtgttttgta cttggaacac ttctcagtgt    60
ggaccagatg catttcacat actcagtagt cacgcgtggc cagtgccttc cataccacac    120
agtgcagcat ctgtagaggt ttcctccact gctgatagac taggagaccc caagatggaa    180
agcctgaaga atctgctcct tgaagtaggg accttaatgg ggtgcacgcc agggcgaccc    240
caagtggtag mctgcttttg aaccatggct atccctacct ctagactcag ctgaaaagaa    300
ctcaggtagt cttgggaagt gcttcctcaa tgcttaaact ttaatgcagg aaaagaatag    360
aaagttcagg caaggaggga ggatcacttg aggctgggag t                       401
```

<210> SEQ ID NO 13
<211> LENGTH: 402
<212> TYPE: DNA
<213> ORGANISM: Homo sapiens -continued

<400> SEQUENCE: 13

```
gcagagagca catcaacaac ccacacgaaa atgtaaatct gagaaataaa tatgcgtggt      60
tggtttaaaa agagaaagaa ttaacattta aagcaatggt aatttactct gatctgtaat     120
tttgagctcc tgtgctgaaa ttgctcattt ggaaattacc aagtgcttgg gtctcatttg     180
tgatcttctt cctgcataca tccagcacac aaaggagtca taatgaccgg ctgagtcact     240
gctgccatct ccctgaagcg tgctcttcaa atgtcaatac cattttctat ggtacaatga     300
agaaaattcc gaattgtagc ctgcttacac taaagggtga gcccgaaaca gcacagaacc     360
tggaatatgc tcaaagggca tcrcaatcct ctcccattct cy                        402
```